(12) United States Patent
Leone et al.

(10) Patent No.: US 12,209,172 B2
(45) Date of Patent: Jan. 28, 2025

(54) CURABLE COMPOSITIONS AND METHODS OF USING THE SAME

(71) Applicant: 3M INNOVATIVE PROPERTIES COMPANY, St. Paul, MN (US)

(72) Inventors: Amanda K. Leone, St. Paul, MN (US); Ahmed S. Abuelyaman, Woodbury, MN (US); Yizhong Wang, Woodbury, MN (US); Wayne S. Mahoney, St. Paul, MN (US); William H. Moser, Edina, MN (US)

(73) Assignee: 3M Innovative Properties Company, St. Paul, MN (US)

(*) Notice: Subject to any disclaimer, the term of this patent is extended or adjusted under 35 U.S.C. 154(b) by 294 days.

(21) Appl. No.: 17/912,021

(22) PCT Filed: Apr. 5, 2021

(86) PCT No.: PCT/IB2021/052816
§ 371 (c)(1),
(2) Date: Sep. 15, 2022

(87) PCT Pub. No.: WO2021/205324
PCT Pub. Date: Oct. 14, 2021

(65) Prior Publication Data
US 2023/0133261 A1 May 4, 2023

Related U.S. Application Data

(60) Provisional application No. 63/006,834, filed on Apr. 8, 2020.

(51) Int. Cl.
| | | |
|---|---|---|
| C08F 2/46 | (2006.01) | |
| A61K 6/62 | (2020.01) | |
| A61K 6/71 | (2020.01) | |
| C08F 2/50 | (2006.01) | |
| C08F 222/10 | (2006.01) | |
| C08G 61/04 | (2006.01) | |
| C08K 3/08 | (2006.01) | |
| C08K 5/08 | (2006.01) | |
| C08L 33/10 | (2006.01) | |

(52) U.S. Cl.
CPC ............... *C08K 5/08* (2013.01); *A61K 6/62* (2020.01); *A61K 6/71* (2020.01); *C08F 2/50* (2013.01); *C08F 222/102* (2020.02); *C08K 3/08* (2013.01); *C08L 33/10* (2013.01); *C08K 2003/0806* (2013.01); *C08K 2201/001* (2013.01)

(58) Field of Classification Search
CPC . A61K 6/71; A61K 6/844; A61K 6/62; A61K 6/30; A61K 6/35; A61K 6/887; C08F 2/50; C08F 222/102; C08F 222/20; C08F 222/346; C08F 222/1025; C08L 33/10; C08L 33/08; C08K 3/08; C08K 5/08; C08K 2003/0806; C08K 2201/001

USPC ............. 522/6, 189, 184, 71, 1; 520/1
See application file for complete search history.

(56) References Cited

U.S. PATENT DOCUMENTS

| | | |
|---|---|---|
| 2,900,360 A | 8/1959 | Robert |
| 4,503,169 A | 3/1985 | Randklev |
| 4,534,839 A | 8/1985 | Schaefer |
| 4,624,910 A | 11/1986 | Takeda |
| 4,695,251 A | 9/1987 | Randklev |
| 5,001,032 A | 3/1991 | Katayama et al. |
| 6,080,389 A | 6/2000 | Sheariss et al. |
| 6,248,804 B1 | 6/2001 | Lutz |
| 6,387,981 B1 | 5/2002 | Zhang et al. |
| 6,572,693 B1 | 6/2003 | Wu et al. |
| 6,730,156 B1 | 5/2004 | Windisch et al. |

(Continued)

FOREIGN PATENT DOCUMENTS

| | | | |
|---|---|---|---|
| EP | 1374830 A1 * | 1/2004 | ........... A61K 6/0017 |
| EP | 2 198 824 A1 | 6/2010 | |

(Continued)

OTHER PUBLICATIONS

Bowman, "Synthesis and photopolymerization of N,N0-dimethyl,-N,N0-di(methacryloxy ethyl)-1,6-hexanediamine as a polymerizable amine coinitiator for dental restorations", Biomaterials, Feb. 2002, vol. 23, No. 4, pp. 1221-1226.

(Continued)

*Primary Examiner* — Jessica Whiteley

(57) ABSTRACT

Curable compositions comprise at least one (meth)acrylate monomer; silver; and a photoinitiator system. The photoinitiator system comprises at least one cyclic β-diketone represented by the formula (I) or a tautomer thereof, wherein: $R^1$ represents H or an organic moiety having from 1 to 32 carbon atoms and optionally 1 to 12 heteroatoms selected from O, N, and combinations thereof; each $R^2$ independently represents H or an aliphatic group having from 1 to 12 carbon atoms, and up to two of oxygen and sulfur atoms; and n represents 1, 2, or 3; and at least one Type II photoinitiator. Methods of making and using the compositions are also disclosed.

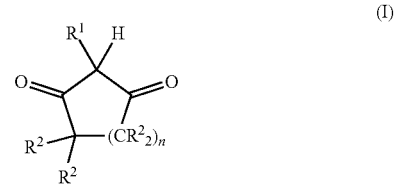

(I)

15 Claims, No Drawings

(56) References Cited

U.S. PATENT DOCUMENTS

| | | |
|---|---|---|
| 7,090,721 B2 | 8/2006 | Craig et al. |
| 7,090,722 B2 | 8/2006 | Budd et al. |
| 7,156,911 B2 | 1/2007 | Kangas |
| 7,241,437 B2 | 7/2007 | Davidson et al. |
| 7,649,029 B2 | 1/2010 | Kolb et al. |
| 8,389,599 B2 | 3/2013 | Yang et al. |
| 10,011,665 B1 | 7/2018 | Miyano et al. |
| 2004/0059124 A1 | 3/2004 | Cyr et al. |
| 2005/0256218 A1 | 11/2005 | Lachowicz et al. |
| 2009/0005026 A1 | 2/2009 | Platzer et al. |
| 2012/0025903 A1 | 10/2012 | Neffgen et al. |

FOREIGN PATENT DOCUMENTS

| | | |
|---|---|---|
| JP | 2011-221192 A | 11/2011 |
| JP | 2012-41465 A | 3/2012 |
| JP | 2015-028179 A | 2/2015 |
| WO | 2001030304 A1 | 5/2001 |
| WO | 2001030305 A1 | 5/2001 |
| WO | 2001030307 A1 | 5/2001 |
| WO | 2003063804 A1 | 8/2003 |
| WO | 2009/098509 A1 | 8/2009 |
| WO | 2021049335 A1 | 3/2021 |

OTHER PUBLICATIONS

Garra, "Metal Acetylacetonate-Bidentate Ligand Interaction (MABLI) (Photo)activated Polymerization: Toward High Performance AmineFree, Peroxide-Free Redox Radical (Photo)initiating Systems", Macromolecules, Mar. 2018, vol. 51, No. 7, pp. 2706-2715.

Garra, "Peroxide-Free and Amine-Free Redox Free Radical Polymerization: Metal Acetylacetonates/Stable Carbonyl Compounds for Highly Efficient Synthesis of Composites", Macromolecules, Aug. 2018, vol. 51, No. 16, pp. 6395-6404.

Green, Industrial Photoinitiators—A Technical Guide, (2010), 86-91.

International Search Report for PCT International Application No. PCT/IB2021/052816, mailed on Jul. 2, 2021, 5 pages.

Kirschner, "Sulfinates and sulfonates as high performance co-initiators in CQ based systems: Towards aromatic amine-free systems for dental restorative materials", Dental Materials, Nov. 2019, vol. 36, No. 2, pp. 187-196.

Matijevic, "Surface & Colloid Science", vol. 6, Wiley Interscience—Table of Content, 1973, 3 pages.

Shi, "A Natural Component as Coinitiator for Unfilled Dental Resin Composites", Journal of Biomedical Materials Research Part B: Applied Biomaterials, Jun. 2007, vol. 82B, No. 1, pp. 44-50.

\* cited by examiner

CURABLE COMPOSITIONS AND METHODS OF USING THE SAME

CROSS-REFERENCE TO RELATED APPLICATIONS

This application is a national stage filing under 35 U.S.C. 371 of PCT/IB2021/052816, filed Apr. 5, 2021, which claims the benefit of U.S. Provisional Application No. 63/006,834, filed Apr. 8, 2020.

TECHNICAL FIELD

The present disclosure broadly relates to curable compositions including a β-diketone and a Type II photoinitiator.

BACKGROUND

Photoinitiated curing is used to produce many industrially important materials such as, for example, coatings, adhesives, restoratives, and sealants. Photoinitiated curing materials typically contain Type I and/or Type II photoinitiators. In each case, the application of light induces rapid curing. Type I photoinitiators fragment when irradiated with the correct wavelength, resulting in polymer-initiating radicals. Type II photoinitiators can abstract H-atoms upon absorption of light, thereby generating initiating radical species. However, if readily abstractable H-atoms are not present then no initiation may occur.

For this reason, Type II photoinitiators are commonly paired with a co-initiator that has abstractable H-atoms to form the photoinitiator system. Common co-initiators are amine-based. However, over time in the presence of oxygen, amine-based co-initiators may oxidize and adversely discolor the resulting material. Additionally, amine-based co-initiators are often acid-sensitive, limiting their utility when acidic adhesion promoting monomers are in the polymerizable composition. Moreover, excess or unused co-initiators may migrate and/or leach out of the cured composition over time.

SUMMARY

Advantageously, the present inventors have discovered compositions containing certain non-amine-based co-initiators that can be used with acidic monomers and can avoid amine-based discoloration.

Further, the compositions include silver which impart a level of antimicrobial protection, and which may make them suitable for medical and dental applications.

In one aspect, the present disclosure provides a curable composition comprising:
at least one (meth)acrylate monomer;
silver; and
a photoinitiator system comprising:
at least one cyclic β-diketone represented by the formula

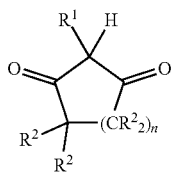

or a tautomer thereof, wherein:
$R^1$ represents H or an organic moiety having from 1 to 32 carbon atoms and optionally 1 to 12 heteroatoms selected from O, N, and combinations thereof;
each $R^2$ independently represents H or an aliphatic group having from 1 to 12 carbon atoms, and up to two of oxygen and sulfur atoms; and
n represents 1, 2, or 3; and
at least one Type II photoinitiator.

In another aspect, the present disclosure provides a curable dental composition comprising: at least one (meth)acrylate monomer;
silver; and
a photoinitiator system comprising:
at least one cyclic β-diketone represented by the formula

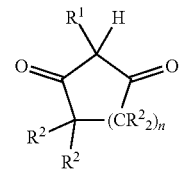

or a tautomer thereof, wherein:
$R^1$ represents H or an organic moiety having from 1 to 32 carbon atoms and optionally 1 to 12 heteroatoms selected from O, N, and combinations thereof;
each $R^2$ independently represents H or an aliphatic group having from 1 to 12 carbon atoms, and up to two of oxygen and sulfur atoms; and
n represents 1, 2, or 3; and
at least one Type II photoinitiator.

In another aspect, the present disclosure provides a method of using a curable dental composition, the method comprising:
contacting the curable dental composition with at least one substrate, wherein the curable dental composition comprises:
at least one (meth)acrylate monomer;
silver; and
a photoinitiator system comprising:
at least one cyclic β-diketone represented by the formula

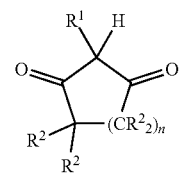

or a tautomer thereof, wherein:
$R^1$ represents H or an organic moiety having from 1 to 32 carbon atoms and optionally 1 to 12 heteroatoms selected from O, N, and combinations thereof;
each $R^2$ independently represents H or an aliphatic group having from 1 to 12 carbon atoms, and up to two of oxygen and sulfur atoms; and n represents 1, 2, or 3; and
at least one Type II photoinitiator; and
exposing the curable dental composition to sufficient actinic electromagnetic radiation to at least partially cure the curable dental composition.

As Used Herein:

The term "Type II photoinitiator" refers to a compound wherein absorption of electromagnetic radiation (e.g., ultraviolet and/or visible light) causes an excited electron state in the Type II photoinitiator that will abstract a hydrogen from the co-initiator, and in the process, generate a radical pair.

The term "dental composition" refers to any composition that can be used in the dental field. By "dental composition" it is meant that an unfilled or filled (e.g., a composite) material (e.g., a dental or orthodontic material) that is capable of being applied or adhered to an oral surface. Dental compositions include, for example, adhesives (e.g., dental and/or orthodontic adhesives), cements (e.g., glass ionomer cements, resin-modified glass ionomer cements, and/or orthodontic cements), primers (e.g., orthodontic primers), restoratives (e.g., a restorative filling material), liners, sealants (e.g., orthodontic sealants), and coatings. Oftentimes a dental composition can be used to bond a dental article to a tooth structure.

The term "essentially free of" in reference to a certain component (e.g., an amine or a metal chelate) means that the composition does not contain said component as an essential feature. Thus, said component is not intentionally added to the composition either as such or in combination with other components or ingredients of other components. A composition being essentially free of a certain component (e.g., a resin) usually contains the component in an amount of less than about 5 weight percent, less than about 1 weight percent, less than about 0.5 weight percent, or less than about 0.01 weight percent, based on the total weight of the composition or material. The composition may not contain said component at all. However, sometimes the presence of a small amount of the said component can be unavoidable, for example, due to impurities contained in the raw materials used.

The term "(meth)acryl" is a shorthand term referring to "acryl" and/or "methacryl." For example, a "(meth)acryloxy" group is a shorthand term referring to an acryloxy group (i.e., $CH_2=CH-C(O)-O-$) and/or a methacryloxy group (i.e., $CH_2=C(CH_3)-C(O)-O-$).

The term "substituted" means replacement of a hydrogen atom with another organic (e.g., alkyl, aryl, alkaryl, or aralkyl), or inorganic group (e.g., halide, hydroxyl, alkoxyl); and The term "metal chelate" refers to a compound between an organic moiety and a metal ion, wherein the metal ion has a formal charge of at least 2+.

Features and advantages of the present disclosure will be further understood upon consideration of the detailed description as well as the appended claims.

DETAILED DESCRIPTION

Curable compositions according to the present disclosure comprise at least one monomer comprising at least one (meth)acryl group, silver, and a photoinitiator system. In many preferred embodiments, the at least one monomer comprises at least two or at least 3 monomers comprising at least one (meth)acryl group.

In many embodiments of the present disclosure, monomers containing methacryl group(s) are preferred over those having acryl groups, although this is not a requirement. In many embodiments, the polymerizable component preferably comprises one or more di-, tri-, tetra- and/or pentafunctional monomeric or oligomeric aliphatic, cycloaliphatic, and/or aromatic (meth)acrylate(s).

(Meth)acryl group-containing monomers are widely commercially available; for example, from Sartomer Co., Exton, Pennsylvania and other vendors. Suitable monomers may include mono-, di- or poly-(meth)acrylates such as, for example, (meth)acrylic acid, 2-(2-ethoxyethoxy)ethyl (meth)acrylate, 2-ethylhexyl (meth)acrylate, 2-hydroxyethyl (meth)acrylate, alkoxylated tetrahydrofurfuryl (meth)acrylate, allyl (meth)acrylate, bis[1-(2-acryloxy)]-p-ethoxyphenyldimethylmethane, bis[1-(3-acryloxy-2-hydroxy)]-p-propoxyphenyldimethylmethane, bis(trimethylolpropane) tetraacrylate, chlorinated polyester (meth)acrylates, diethylene glycol di(meth)acrylate, diglycidyl (meth)acrylate of bisphenol A, dodecyl (meth)acrylate, epoxy (meth)acrylate oligomers, ethoxylated or propoxylated glycerol tri(meth)acrylate, ethyl (meth)acrylate, ethylene glycol di(meth)acrylate, glycerol di(meth)acrylate, glycerol tri(meth)acrylate, hexanediol di(meth)acrylate, hexyl (meth)acrylate, hydroxybutyl (meth)acrylate, hydroxy-functional caprolactone ester (meth)acrylate, hydroxyisopropyl (meth)acrylate, hydroxymethyl (meth)acrylate, hydroxypropyl (meth)acrylate, isobornyl (meth)acrylate, isobutyl (meth)acrylate, isodecyl (meth)acrylate, isononyl (meth)acrylate, isooctyl (meth)acrylate, isopropyl (meth)acrylate, lauryl (meth)acrylate, methyl (meth)acrylate, n-butyl (meth)acrylate, neopentyl glycol di(meth)acrylate, n-hexyl (meth)acrylate, nonylphenol ethoxylate (meth)acrylate, octyl (meth)acrylate, pentaerythritol tetra(meth)acrylate, pentaerythritol triacrylate, poly(ethylene glycol) di(meth)acrylates, polybutadiene di(meth)acrylates, polyester (meth)acrylate oligomers, polyurethane di(meth)acrylates, silicone (meth)acrylate oligomers, sorbitol hexaacrylate, stearyl (meth)acrylate, tetraethylene glycol di(meth)acrylate, tetrahydrofurfuryl (meth)acrylate, triethylene glycol di(meth)acrylate, tris(hydroxyethyl) isocyanurate tri(meth)acrylate, β-carboxyethyl (meth)acrylate, 1,1,1-trimethylolpropane tri(meth)acrylate, 1,2,4-butanetriol tri(meth)acrylate, hexane-2,4,6-triol tri(meth)acrylate, 1,3-propanediol di(meth)acrylate, 1,4-cyclohexanediol diacrylate, 1,6-hexanediol di(meth)acrylate, 1,12-dodecanediol di(meth)acrylate, (meth)acrylamide, N,N-dimethyl(meth)acrylamide, methylene bis-(meth)acrylamide, diacetone (meth)acrylamide and combinations thereof.

The monomer containing at least one (meth)acryl group is typically present in the composition in an amount of at least 40, at least 50, at least 60, at least 70, at least 80, at least 90, at least 95, or even at least 98 weight percent, based on the total weight of the composition, although this is not a requirement.

The free-radically polymerizable compound(s) may comprise an acid-functional monomer, where the acid functional group may be an acid per se, such as a carboxylic acid, or a portion may be a salt thereof, such as an alkali metal carboxylate. Useful acid functional monomers include, but are not limited to, those selected from ethylenically-unsaturated carboxylic acids, ethylenically-unsaturated sulfonic acids, ethylenically-unsaturated phosphonic or phosphoric acids, and mixtures thereof. Examples of such compounds include those selected from acrylic acid, methacrylic acid, itaconic acid, fumaric acid, crotonic acid, citraconic acid, maleic acid, oleic acid, β-carboxyethyl (meth)acrylate, 2-sulfoethyl methacrylate, styrenesulfonic acid, 2-acrylamido-2-methylpropanesulfonic acid, vinylphosphonic acid, phosphate esters of polypropylene glycol monomethacrylate, and mixtures thereof. Due to their availability, acid-functional monomers are typically selected from ethylenically unsaturated carboxylic acids (e.g., (meth)acrylic acids). When stronger acids are desired, acidic monomers may include ethylenically-unsaturated sulfonic acids and ethylenically-unsaturated phosphonic acids. If present, acid-functional monomer is typically used in amounts of 0.5 to 15 parts by weight, preferably 1 to 15 parts by weight, most preferably 5 to 10 parts by weight, based on 100 parts by weight total monomer, although this is not a requirement.

The photoinitiator system comprises at least one cyclic β-diketone in combination with a Type II photoinitiator.

Useful cyclic β-diketone(s) are represented by the formula

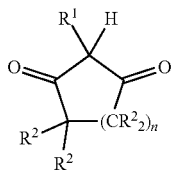

or a tautomer thereof (e.g., as shown below):

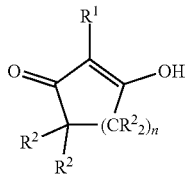

wherein $R^1$ represents H or an organic moiety having from 1 to 32 carbon atoms and optionally 1 to 12 heteroatoms selected from O, N, and combinations thereof. In some preferred embodiments, $R^1$ has 4 to 20 carbon atoms, and optionally contains 1 to 12 heteroatoms selected from O, N, and combinations thereof. In some preferred embodiments, $R^1$ has 4 to 16 carbon atoms, and optionally contains 1 to 8 heteroatoms selected from O, N, and combinations thereof. In some preferred embodiments, $R^1$ has 4 to 12 carbon atoms, and optionally contains 1 to 8 heteroatoms selected from O, N, and combinations thereof. In some preferred embodiments, $R^1$ has 4 to 8 carbon atoms, and optionally contains 1 to 6 heteroatoms selected from O, N, and combinations thereof. In some preferred embodiments, $R^1$ has 4 to 6 carbon atoms, and optionally contains 1 to 4 heteroatoms selected from O, N, and combinations thereof. Exemplary organic moieties $R^1$ are exemplified in the Examples contained hereinbelow. Other examples of organic moieties $R^1$ may include alkyl groups having from 1 to 12 carbon atoms (e.g., methyl, ethyl, propyl, isopropyl, butyl, hexyl, octyl, decyl, dodecyl, hexadecyl, cyclohexyl, methylcyclohexyl, or octadecyl), alkoxyalkyl groups having from 2 to 8 carbon atoms (e.g., methoxymethyl, ethoxymethyl, ethoxyethyl or butoxybutyl), phenyl, benzyl, phenethyl, a monovalent aliphatic polyether, or a monovalent aromatic polyether. In some embodiments, $R^1$ represents H or an alkyl group having from 1 to 12 carbon atoms, preferably 1 to 8 carbon atoms, more preferably 1 to 4 carbon atoms, and more preferably 1 or 2 carbon atoms (e.g., methyl ethyl).

Each $R^2$ independently represents H or an aliphatic group having from 1 to 12 carbon atoms (preferably 1 to 8, more preferably 1 to 4, and more preferably 1 or 2 carbon atoms), and up to two of oxygen and sulfur atoms. In many preferred embodiments, $R^2$ represents an alkyl group having from 1 to 4 carbon atoms, more preferably methyl or ethyl.

n represents 1, 2, or 3, more preferably 1 or 2.

Combinations of cyclic β-diketones may also be used.

Cyclic β-diketones can be prepared, for example, according to known methods and/or obtained from chemical suppliers such as, for example, MilliporeSigma, Saint Louis, Missouri. Examples include 1,3-cyclohexanedione, 5,5-dimethyl-1,3-cyclohexanedione, 2-methyl-1,3-cyclohexanedione, 1,3-cyclopentanedione, 1,3-cycloheptanedione, 2-methyl-1,3-cyclopentanedione, 4,4-dimethyl-1,3-cyclohexanedione, 5-phenyl-1,3-cyclohexanedione, 5-methyl-1,3-cyclohexanedione, 5-[4-(methoxyphenyl)]-1,3-cyclohexanedione, 1,3-cycloheptanedione, 4-methyl-1,3-cycloheptanedione.

Suitable Type II photoinitiators are well known in the photocuring art. Type II photoinitiators of commercial importance include: diaryl ketones (e.g., benzophenone, 4-methylbenzophenone, or 4-chlorobenzophenone); 1-phenylpropane-1,2-dione (PPD); thioxanthones (2-isopropylthioxanthone, 2-mercaptothioxanthone, 2,4-diethylthioxanthone (DETX), 1-chloro-4-propoxythioxanthone (CPTX), and 2-chlorothioxanthone (CTX), or 4-isopropylthioxanthone); camphorquinone; benzil; naphthoquinones (e.g., 2,2'-bis (3-hydroxy-1,4-naphthoquinone)), anthraquinones (e.g., anthraquinone, 1,4-dihydroxyanthraquinone, 2-methylanthraquinone, or 2,6-dihydroxyanthraquinone), and 3-ketocoumarins or a combination thereof. Other Type II photoinitiators are described in Green, A. W. (2010). Commercial Photoinitiators. *Industrial Photoinitiators, A Technical Guide* (pp. 86-91). CRC Press, Taylor and Francis Group.

The absorption characteristics of the Type II photoinitiator(s) will typically be selected depending at least in part on the desired wavelengths of the actinic radiation selected. Generally, the actinic radiation will be in the ultraviolet (i.e., 200 to less than 400 nanometers) and/or visible (i.e., 400 to 700 nanometers) wavelength range, although this is not a requirement. A preferred wavelength range is 250 to 450 nanometers.

The photoinitiator systems may be used in any amount, preferably 0.01 to 10 weight percent, more preferably 0.1 to 5 weight percent, and more preferably 0.1 to 2 weight percent, based on the total weight of the curable composition. The weight ratio of the cyclic β-diketone and the Type II photoinitiator will vary with the materials selected, but is within the capability of those of ordinary skill in the art.

As discussed earlier, amines may give rise to aesthetically unacceptable discoloration overtime. Accordingly, in many preferred embodiments the curable composition is essentially free of, or free of, organic amines. Likewise, the curable composition is preferably essentially free of, or free of, polyvalent metal complexes of β-diketones (cyclic and/or non-cyclic) that may also result in coloration.

Curable compositions according to the present disclosure may contain silver (e.g., in the form of silver salts, colloidal silver, or silver oxide). Examples of suitable silver salts include silver chloride, silver bromide, silver iodide, silver acetate, silver propionate, silver fluoride, silver nitrate, silver thiocyanate, silver diamine fluoride, silver iodide complex compound, silver phosphate, or a combination thereof.

Compositions according to the present disclosure may contain filler (i.e., one or more filler). Fillers can be chosen to enhance certain properties, such as compressive strength, diametral tensile strength, wear resistance, appearance, translucency, radiopacity, and storage stability of the dental materials, as well as to limit exothermic effects during the initial set phase. Optionally, the surface of the filler particles may be treated with a surface treatment, such as a silane coupling agent, in order to enhance the bond between the filler and the resin system. The coupling agent may be functionalized with reactive curing groups, such as acrylates and/or methacrylates. Fillers may be selected from one or more of a wide variety of materials suitable for incorporation in compositions used for dental applications, such as fillers currently used in dental restorative compositions, for example.

The filler can be an inorganic material. Examples of suitable inorganic fillers include naturally occurring or synthetic materials such as quartz, nitrides (e.g., silicon nitride), glasses derived from, for example, Ce, Sb, Sn, Zr, Sr, Ba, or Al, colloidal silica, feldspar, borosilicate glass, kaolin, talc, titania, zirconia, and zinc glass, zirconia-silica fillers; low Mohs hardness fillers such as those described in U.S. Pat. No. 4,695,251 (Randklev); and submicron silica particles (e.g., pyrogenic silicas such as those available under the trade designation "AEROSIL" such as "OX 50," "AEROSIL 130," "AEROSIL 200," "AEROSIL 380," from Evonik, Parsippany, New Jersey and "Cab-O-Sil M5" silica from Cabot Corp., Boston, Massachusetts). Non-acid-reactive inorganic filler particles include quartz (i.e., silica), submicron silica, zirconia, submicron zirconia, and non-vitreous microparticles of the type described in U.S. Pat. No. 4,503,169 (Randklev). The filler can be a crosslinked organic material that is insoluble in the polymerizable resin and is optionally filled with inorganic filler. The filler is generally non-toxic and suitable for use in the mouth. The filler can be radiopaque, radiolucent, or nonradiopaque. Fillers as used in dental applications are typically ceramic in nature.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses either untreated or silanol treated, can be used. The FAS glasses have the added benefit of releasing fluoride at the site of dental work when placed in the oral environment. The FAS glass typically contains sufficient elutable cations so that a hardened dental composition will form when the glass is mixed with the components of the hardenable composition. The glass also typically contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation particle size analyzer. Suitable FAS glasses will be familiar to those skilled in the art, and are available from a wide variety of commercial sources, and many are found in currently available glass ionomer cements such as those commercially available under the trade designations VITREMER, VITREBOND, RELYX LUTING CEMENT, RELYX LUTING PLUS CEMENT, PHOTAC FIL QUICK APLICAP, KETAC-MOLAR, and KETAC-FIL PLUS (3M ESPE Dental Products, St. Paul, Minnesota), FUJI II LC and FUJI IX (GC Corporation, Tokyo, Japan) and CHEMFIL Superior (Dentsply International, York, Pennsylvania). Mixtures of fillers can be used if desired.

Other suitable fillers are disclosed in U.S. Pat. No. 6,387,981 (Zhang et al.) and U.S. Pat. No. 6,572,693 (Wu et al.) as well as PCT International Publication Nos. WO 01/30305 (Zhang et al.), U.S. Pat. No. 6,730,156 (Windisch et al.), WO 01/30307 (Zhang et al.), and WO 03/063804 (Wu et al.). Filler components described in these references include nanosized silica particles, nanosized metal oxide particles, and combinations thereof. Nanofillers are also described in U.S. Pat. No. 7,090,721 (Craig et al.), U.S. Pat. No. 7,090,722 (Budd et al.), and U.S. Pat. No. 7,156,911 (Kangas et al.); and U.S. Pat. No. 7,649,029 (Kolb et al.).

Examples of suitable organic filler particles include filled or unfilled pulverized polycarbonates, polyepoxides and poly(meth)acrylates, for example. Commonly employed dental filler particles are quartz, submicron silica, and non-vitreous microparticles of the type described in U.S. Pat. No. 4,503,169 (Randklev).

Mixtures of these fillers can also be used, as well as combination fillers made from organic and inorganic materials.

Fillers may be either particulate or fibrous in nature. Particulate fillers may generally be defined as having a length to width ratio, or aspect ratio, of 20:1 or less, and more commonly 10:1 or less. Fibers can be defined as having aspect ratios greater than 20:1, or more commonly greater than 100:1. The shape of the particles can vary, ranging from spherical to ellipsoidal, or more planar such as flakes or discs. The macroscopic properties can be highly dependent on the shape of the filler particles and in particular, the uniformity of the shape. Suitable optional fillers may be finely divided with an average particle size (i.e., the longest dimension of the particle, such as the diameter) of no greater than about 10 micrometers and a maximum particle size of no greater than about 50 micrometers, although this is not a requirement. The filler can have a unimodal or polymodal (e.g., bimodal) particle size distribution.

In some preferred embodiments, the dental composition comprises silica nanoparticles. Suitable nano-sized silicas are commercially available from Nalco Chemical Co., Naperville, Illinois under the product designation NALCO COLLOIDAL SILICAS. For example, preferred silica particles can be obtained from using NALCO products 1040, 1042, 1050, 1060, 2327 and 2329.

Silica particles are preferably made from an aqueous colloidal dispersion of silica (i.e., a sol or aquasol). The colloidal silica is typically in the concentration of about 1 to 50 weight percent in the silica sol. Colloidal silica sols that can be used are available commercially having different colloid sizes, see Matijevic, E. Surface & Coiloid Science, Vol. 6, ed. Wiley, John Sons, 1973. Preferred silica sols for use making the fillers are supplied as a dispersion of amorphous silica in an aqueous medium (such as the Nalco colloidal silicas made by Nalco Chemical Co.) and those which are low in sodium concentration and can be acidified by admixture with a suitable acid (e.g., LUDOX colloidal silica made by E. I. Dupont de Nemours & Co. or NALCO 2326 from Nalco Chemical Co.). Preferably, the silica particles in the sol have an average particle diameter of about 5-100 nanometers (nm), more preferably 10-50 nm, and most preferably 12-40 nm.

In some embodiments, the dental composition comprises zirconia nanoparticles. Suitable nano-sized zirconia nanoparticles can be prepared using hydrothermal technology as described in U.S. Pat. No. 7,241,437 (Davidson et al.).

In some embodiments, the total amount of filler is about 2 weight percent to about 90 weight percent, based on the total weight of the components of the dental material. In certain embodiments, the total amount of filler is about 30 weight percent to about 85 weight percent, based on the total weight of the components of the dental material. Optional filler may be present any suitable amount (e.g., 10 to 90 weight percent of the curable composition, preferably 10 to 60 weight percent of the curable composition).

Curable compositions according to the present disclosure may include one or more additional components such as, for example, solvent, antioxidants, flavorants, fluoridating agents, buffering agents, numbing agents, remineralization agents, desensitization agents, colorants, indicator(s), viscosity modifiers, surfactants, stabilizers, preservative agents (e.g., benzoic acid), or a combination thereof.

Curable compositions according to the present disclosure may be useful as dental compositions. Dental compositions are typically hardenable compositions that can be hardened at ambient conditions, including a temperature range from about 15 to 50° C. or from about 20 to 40° C. within a time frame of about 30 minutes or 20 minutes or 10 minutes or 1 minute or less. Higher temperatures are not recommended as they might cause pain to a patient and may be detrimental to the patient's health. Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is within these ranges.

Curable compositions according to the present disclosure may be applied to at least one substrate and then cured using actinic radiation. Exemplary sources of radiation include, LED lights (e.g., at 365 nm, 385 nm, 405 or 450 nm for example), arc lamps (e.g., Hg or Xe arc lamps), flash lamps (e.g., Xe flash lamps), ultraviolet lasers or visible wavelength lasers (e.g., excimer lasers, solid state lasers, pulsed and/or CW lasers), and microwave driven H-type, D-type, or V-type mercury lamps (e.g., as marketed by Heraeus Noblelight America, Gaithersburg, Maryland). Filters and/or dichroic reflectors may also be useful, for example, to reduce thermal energy that accompanies the actinic radiation. The selection of curing conditions is within the capability of one of ordinary skill in the art.

Exemplary substrates may comprise metal, glass, ceramic, wood, plastic, fiber composite, tooth enamel and/or dentin, and combinations thereof.

Select Embodiments of the Disclosure

In a first embodiment, the present disclosure provides a curable composition comprising:
at least one (meth)acrylate monomer;
silver; and
a photoinitiator system comprising:
at least one cyclic β-diketone represented by the formula

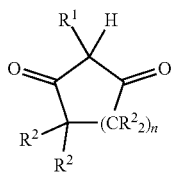

or a tautomer thereof, wherein:
R$^1$ represents H or an organic moiety having from 1 to 32 carbon atoms and optionally 1 to 12 heteroatoms selected from O, N, and combinations thereof;
each R$^2$ independently represents H or an aliphatic group having from 1 to 12 carbon atoms, and up to two of oxygen and sulfur atoms; and
n represents 1, 2, or 3; and
at least one Type II photoinitiator.

In a second embodiment, the present disclosure provides a curable composition according to the first embodiment, wherein the curable composition is free of organic amine.

In a third embodiment, the present disclosure provides a curable composition according to the first or second embodiment, wherein the curable composition is free of polyvalent metal complexes of the at least one cyclic β-diketone.

In a fourth embodiment, the present disclosure provides a curable composition according to any of the first to third embodiments, wherein the at least one Type II photoinitiator comprises at least one of camphorquinone or isopropylthioxanthone.

In a fifth embodiment, the present disclosure provides a curable composition according to any of the first to fourth embodiments, further comprising filler.

In a sixth embodiment, the present disclosure provides a method of using a curable composition, the method comprising:
contacting the curable composition of claim 1 with a at least one substrate; and exposing the curable composition to sufficient actinic electromagnetic radiation to provide an at least partially cured composition.

In a seventh embodiment, the present disclosure provides a curable dental composition comprising:
at least one (meth)acrylate monomer;
silver; and
a photoinitiator system comprising:
at least one cyclic β-diketone represented by the formula

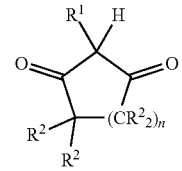

or a tautomer thereof, wherein:
R$^1$ represents H or an organic moiety having from 1 to 32 carbon atoms and optionally 1 to 12 heteroatoms selected from O, N, and combinations thereof;
each R$^2$ independently represents H or an aliphatic group having from 1 to 12 carbon atoms, and up to two of oxygen and sulfur atoms; and
n represents 1, 2, or 3; and
at least one Type II photoinitiator.

In an eighth embodiment, the present disclosure provides a curable dental composition according to the seventh embodiment, wherein the curable dental composition is free of organic amine.

In a ninth embodiment, the present disclosure provides a curable dental composition according to the seventh or eighth embodiment, wherein the curable dental composition is free of metal complexes of the at least one cyclic β-diketone.

In a tenth embodiment, the present disclosure provides a curable dental composition according to any of the seventh to ninth embodiments, wherein the at least one Type II photoinitiator comprises at least one of camphorquinone or isopropylthioxanthone.

In an eleventh embodiment, the present disclosure provides a curable dental composition according to any of the seventh to tenth embodiments, further comprising fillers.

In a twelfth embodiment, the present disclosure provides a method of using a curable dental composition, the method comprising:
  contacting the curable dental composition with at least one substrate, wherein the curable dental composition comprises:
    at least one (meth)acrylate monomer;
    silver; and
    a photoinitiator system comprising:
      at least one cyclic β-diketone represented by the formula

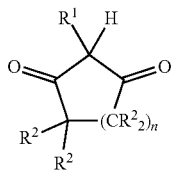

or a tautomer thereof, wherein:
      $R^1$ represents H or an organic moiety having from 1 to 32 carbon atoms and optionally 1 to 12 heteroatoms selected from O, N, and combinations thereof;
      each $R^2$ independently represents H or an aliphatic group having from 1 to 12 carbon atoms, and up to two of oxygen and sulfur atoms; and
      n represents 1, 2, or 3; and
    at least one Type II photoinitiator; and
  exposing the curable dental composition to sufficient actinic electromagnetic radiation to provide and at least partially cured dental composition.

In a thirteenth embodiment, the present disclosure provides a method according to the twelfth embodiment, wherein the curable dental composition is free of organic amine.

In a fourteenth embodiment, the present disclosure provides a method according to the twelfth or thirteenth embodiment, wherein the curable dental composition is free of polyvalent metal complexes of the at least one cyclic β-diketone.

In a fifteenth embodiment, the present disclosure provides a method according to any of the twelfth to fourteenth embodiments, wherein the at least one Type II photoinitiator comprises at least one of camphorquinone or isopropylthioxanthone.

In a sixteenth embodiment, the present disclosure provides a method according to any of the twelfth to fifteenth embodiments, further comprising filler.

In a seventeenth embodiment, the present disclosure provides an at least partially cured composition prepared according to any of the first to sixth embodiments.

In an eighteenth embodiment, the present disclosure provides an at least partially cured dental composition prepared according to any of the twelfth to sixteenth embodiments.

EXAMPLES

Unless otherwise noted, all parts, percentages, ratios, etc. in the Examples and the rest of the specification are by weight.

Materials used in the Examples are listed in TABLE 1, below.

TABLE 1

| Abbreviation | Description and Source |
|---|---|
| DCMA | 2-(((4-((2,6-dioxocyclo-hexyl)methyl)phenoxy)carbonyl)amino)ethyl methacrylate, synthesized as described herein |
| DOH | 2-(4-hydroxybenzyl)cyclohexane-1,3-dione, synthesized as described herein |
| 1,3-cyclohexanedione | Obtained from Alfa Aesar, Ward Hill, Massachusetts |
| 4-hydroxy-benzaldehyde | Obtained from Alfa Aesar, Ward Hill, Massachusetts |
| L-Proline | Obtained from Alfa Aesar, Ward Hill, Massachusetts |
| NaBH$_3$CN | Sodium cyanoborohydride, obtained from Alfa Aesar, Ward Hill, Massachusetts |
| IEM | 2-Isocyanatoethyl methacrylate, obtained from TCI America, Portland, Oregon |
| CPQ | Camphorquinone, obtained from Oakwood Products, Inc., Estill, South Carolina |
| ITX | Isopropylthioxanthone, obtained from TCI America, Portland, Oregon |
| EDMAB | Ethyl 4-dimethylaminobenzoate, obtained from MilliporeSigma, Saint Louis, Missouri |
| HEMA | 2-hydroxyethyl methacrylate, obtained from ESSTECH, Inc., Essington, Pennsylvania |
| BisGMA | Bisphenol A-glycidyl methacrylate CAS Reg. No. 1565-94-2, obtained from 3M OCSD, Irvine, California |
| TEGDMA | Triethylene glycol dimethacrylate, obtained from Sartomer Co., Exton Pennsylvania |
| GDMA | Glycerol dimethacrylate, obtained from Sigma Aldrich, Saint Louis, Missouri |
| Procrylat K | 2,2,-bis-4-(3-hydroxy-propoxy-phenyl)propane dimethacrylate (as further described in US8389599), obtained from 3M OCSD, Seefeld, Germany |
| DDDMA | 1, 12-dodecanediol dimethacrylate, obtained as "SR262" from Sartomer Co., Exton, Pennsylvania |
| BHT | 2,6-di-tert-butyl-4-methylphenol, can obtained from Oakwood Products, Inc., Estill, South Carolina |
| AgI | Silver iodide, obtained from MilliporeSigma, Saint Louis Missouri |
| NH$_4$I | Ammonium iodide, obtained from Honeywell Specialty Chemical, Seelze, Germany |
| NH$_4$F | Ammonium fluoride, obtained from Honeywell Specialty Chemical, Seelze, Germany |

Synthesis of 2-(4-hydroxybenzyl)cyclohexane-1,3-dione (DOH)

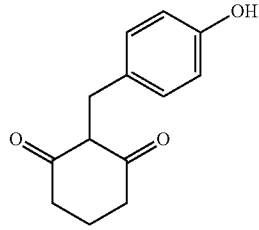 [SMILES: O=C1CCCC(=O)C1Cc1ccc(O)cc1]

To a round bottom flask was added 1,3-cyclohexanedione (32.02 g, 1.000 equiv), 4-hydroxybenzaldehyde (34.85 g, 1.000 equiv), L-proline (13.15 g, 0.4000 equiv) and ethanol (1.428 L). The reaction was stirred for 45 min at room temperature. Then, NaBH₃CN (17.95 g, 1.000 equiv) was added in 2 g portions over 10 min. The heterogeneous mixture was heated to 80° C. and stirred for 18 h. Most of the ethanol was removed under reduced pressure, yielding an orange viscous oil which was dissolved in ethyl acetate (200 mL), quenched with aq. HCl (1M, 200 mL) and stirred until bubbling ceased. The organic layer was separated and washed with aq. HCl (1M, 3×100 mL) and brine (2×100 mL). The organic layer was collected, dried over anhydrous magnesium sulfate, filtered, and concentrated under reduced pressure yielding an orange oil which was crystallized from hot ethyl acetate (100 mL), yielding DOH as a pale orange solid (25.9 g).

Synthesis of 2-(((4-((2,6-dioxocyclohexyl)methyl)phenoxy)carbonyl)amino)ethyl methacrylate (DCMA)

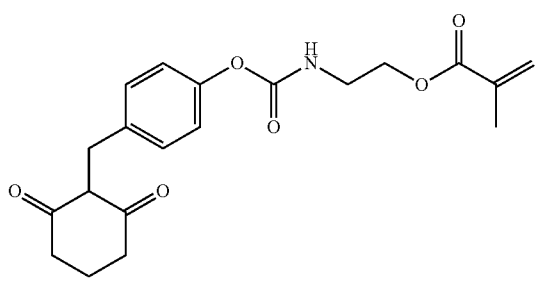 [SMILES: C=C(C)C(=O)OCCNC(=O)Oc1ccc(CC2C(=O)CCCC2=O)cc1]

In a flask equipped with a stirbar, DOH (5.00 g, 1.00 equiv) was dissolved in dry tetrahydrofuran (60 mL) and stirred for 2 min. Triethylamine (3.19 mL, 1.00 equiv) was then added causing some precipitate to form. The mixture was stirred for an additional 2 min then IEM (3.24 mL, 1.00 equiv) and BHT (224 mg) were added and stirred for 60 min at room temperature. Then, the orange solution was concentrated under house air over night (18 h) yielding an orange viscous oil which was purified by column chromatography using a gradient eluent from 80/20 to 20/80 hexanes/ethyl acetate (v/v). The desired fractions were collected, BHT (10 mg) was added and the solvent was removed under reduced pressure yielding DCMA as a white powder (3.39 g).

Examples EX-1 and EX-2 and Comparative Examples CE-A to CE-D

For the following examples, materials were combined to create the inventive examples and comparative examples in the tables below. An aliquot of the formulations was placed on a glass slide, irradiated with then exposed to a blue LED light using 3M ELIPAR DEEPCURE-S LED curing light, (available from 3M Company) with maximum wavelength 450 nm and output approximately 1500 mW/cm² for 20 seconds at an approximate distance of 1 to 5 centimeters, and evaluated immediately by poking with a wooden spatula to determine whether the formulation had cured (hard, brittle solid), were partially cured (forming a gel), or remained uncured (liquid).

TABLE 2

| MATERIAL | CE-A | CE-B | CE-C | EX-1 | CE-D | EX-2 |
| --- | --- | --- | --- | --- | --- | --- |
| DCMA | 0.00 | 0.00 | 1.96 | 1.81 | 1.96 | 1.77 |
| CPQ | 0.24 | 0.24 | 0.23 | 0.22 | 0.23 | 0.21 |
| EDMAB | 0.40 | 0.48 | | | | |
| HEMA | 39.60 | 29.70 | 48.91 | 45.28 | | |
| BisGMA | 8.30 | 29.70 | 48.91 | 45.28 | 27.91 | 25.21 |
| TEGDMA | 3.60 | | | | | |
| GDMA | 7.90 | | | | | |
| Procrylat K | | | | | 55.81 | 50.43 |
| DDDMA | | | | | 13.96 | 12.61 |
| BHT | | | | | 0.14 | 0.13 |
| AgI | 12.44 | 12.38 | | 2.30 | | 3.00 |
| NH₄I | 12.56 | 12.50 | | 2.32 | | 3.03 |
| NH₄F | 1.96 | 1.95 | | 0.36 | | 0.47 |
| Water | 13.08 | 13.01 | | 2.42 | | 3.15 |
| Result | uncured | uncured | cured | partially cured | cured | cured |

The preceding description, given in order to enable one of ordinary skill in the art to practice the claimed disclosure, is not to be construed as limiting the scope of the disclosure, which is defined by the claims and all equivalents thereto.

What is claimed is:

1. A curable composition comprising:
   at least one (meth)acrylate monomer;
   silver; and
   a photoinitiator system comprising:
   at least one cyclic β-diketone represented by the formula

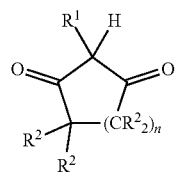

or a tautomer thereof, wherein:
   R¹ represents H or an organic moiety having from 1 to 32 carbon atoms and optionally 1 to 12 heteroatoms selected from O, N, and combinations thereof;
   each R² independently represents H or an aliphatic group having from 1 to 12 carbon atoms, and up to two of oxygen and sulfur atoms; and
   n represents 1, 2, or 3; and
   at least one Type II photoinitiator.

2. The curable composition of claim 1, wherein the curable composition is free of organic amine.

3. The curable composition of claim 1, wherein the curable composition is free of polyvalent metal complexes of the at least one cyclic β-diketone.

4. The curable composition of claim 1, wherein the at least one Type II photoinitiator comprises at least one of camphorquinone or isopropylthioxanthone.

5. The curable composition of claim 1, further comprising fillers.

6. A method of using a curable composition, the method comprising:
contacting the curable composition of claim 1 with a at least one substrate; and exposing the curable composition to sufficient actinic electromagnetic radiation to provide an at least partially cured composition.

7. A curable dental composition comprising:
at least one (meth)acrylate monomer;
silver; and
a photoinitiator system comprising:
at least one cyclic β-diketone represented by the formula

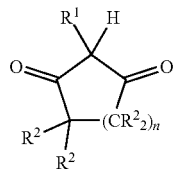

or a tautomer thereof, wherein:
$R^1$ represents H or an organic moiety having from 1 to 32 carbon atoms and optionally 1 to 12 heteroatoms selected from O, N, and combinations thereof;
each $R^2$ independently represents H or an aliphatic group having from 1 to 12 carbon atoms, and up to two of oxygen and sulfur atoms; and
n represents 1, 2, or 3; and
at least one Type II photoinitiator.

8. The curable dental composition of claim 7, wherein the curable dental composition is free of organic amine.

9. The curable dental composition of claim 7, wherein the curable dental composition is free of metal complexes of the at least one cyclic β-diketone.

10. The curable dental composition of claim 7, wherein the at least one Type II photoinitiator comprises at least one of camphorquinone or isopropylthioxanthone.

11. The curable dental composition of claim 7, further comprising fillers.

12. A method of using a curable dental composition, the method comprising:
contacting the curable dental composition with at least one substrate, wherein the curable dental composition comprises:
at least one (meth)acrylate monomer;
silver; and
a photoinitiator system comprising:
at least one cyclic β-diketone represented by the formula

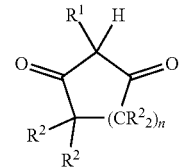

or a tautomer thereof, wherein:
$R^1$ represents H or an organic moiety having from 1 to 32 carbon atoms and optionally 1 to 12 heteroatoms selected from O, N, and combinations thereof;
each $R^2$ independently represents H or an aliphatic group having from 1 to 12 carbon atoms, and up to two of oxygen and sulfur atoms; and
n represents 1, 2, or 3; and
at least one Type II photoinitiator; and
exposing the curable dental composition to sufficient actinic electromagnetic radiation to at least partially cure the curable dental composition.

13. The method of claim 12, wherein the curable dental composition is free of organic amine.

14. The method of claim 12, wherein the curable dental composition is free of polyvalent metal complexes of the at least one cyclic β-diketone.

15. The method of claim 12, wherein the at least one Type II photoinitiator comprises at least one of camphorquinone or isopropylthioxanthone.

* * * * *